United States Patent [19]

Williams

[11] 4,168,204
[45] Sep. 18, 1979

[54] STABLE FREEZE-DRIED LOWENSTEIN-JENSEN MEDIUM AND A METHOD FOR ITS PREPARATION

[75] Inventor: Wilmore Williams, Wheaton, Ill.
[73] Assignee: Beatrice Foods Co., Chicago, Ill.
[21] Appl. No.: 801,329
[22] Filed: May 27, 1977

Related U.S. Application Data

[63] Continuation-in-part of Ser. No. 659,703, Feb. 20, 1976, Pat. No. 4,072,570, which is a continuation of Ser. No. 243,078, Apr. 11, 1972, abandoned.

[51] Int. Cl.$^2$ .............................................. C12K 1/00
[52] U.S. Cl. .......................................... 435/34; 34/5
[58] Field of Search ................ 195/100, 101, 96, 104, 195/103.5 M; 426/384, 385; 34/5

[56] References Cited

U.S. PATENT DOCUMENTS

| | | | |
|---|---|---|---|
| 2,970,948 | 2/1961 | Stevens | 195/102 |
| 3,009,818 | 11/1961 | Jokay et al. | 426/385 |
| 3,075,887 | 1/1963 | Silliker | 195/100 |
| 3,360,440 | 12/1967 | Haab | 195/102 |
| 3,616,258 | 10/1971 | Kronish et al. | 195/103.5 M |
| 4,035,238 | 7/1977 | Meyer et al. | 195/103.5 M |
| 4,072,570 | 2/1978 | Williams | 195/100 |

OTHER PUBLICATIONS

BBL Manual of Products and Laboratory Procedures, 5th Ed., (1968), BioQuest, Division of Becton, Dickinson and Company, pp. 118, 119.
Difco Manual, 9th Ed., Difco Laboratories, Detroit, Michigan, (1968), p. 209.
Cunningham, "Egg Product Pasteurization", Egg Science and Technology, Stadelman ed., Company, Inc. The Avi Publishing Company, Inc., Conn., (1973), pp. 153–198, 208, 209–212.
Johnson, et al., Encyclopedia of Food Technology, The Avi Publishing Co., Inc., Wesport, Conn., (1974), pp. 358, 359.

Primary Examiner—Thomas G. Wiseman
Attorney, Agent, or Firm—Murray and Whisenhunt

[57] ABSTRACT

A storage stable Lowenstein-Jensen medium is prepared by freeze drying the liquid medium to provide a powder having a moisture content of less than 8% by weight. The dried powder is stable at ambient temperature for at least one year and may be easily reconstituted to the fluid Lowenstein-Jensen medium by simple mixing at ambient conditions.

10 Claims, No Drawings

STABLE FREEZE-DRIED LOWENSTEIN-JENSEN MEDIUM AND A METHOD FOR ITS PREPARATION

This is a continuation-in-part of pending U.S. application Ser. No. 659,703, filed on Feb. 20, 1976, now U.S. Pat. No. 4,072,570, which is in turn a continuation of application Ser. No. 243,078, filed on Apr. 11, 1972, now abandoned.

The present invention relates to a growth medium for tuberculosis organisms, and more particularly to a medium which may be stored under ambient conditions for extended periods of time without degradation or other deterioration thereof.

BACKGROUND OF THE INVENTION

The detection of the disease tuberculosis is usually performed by culturing a specimen from a suspected host in a medium referred to in the art as the Lowenstein-Jensen medium, or modifications thereof. The culture is incubated and the *M. tuberculosis* organisms develop to the substantial exclusion of other organisms. Thus, a positive test for tuberculosis is provided.

While this test is quite accurate and is widely practiced, the test has a decided disadvantage in that the Lowenstein-Jensen medium is not storage stable at ambient temperatures and even when refrigerated must be used within 30 days of preparation. In view thereof, it has been the practice in the art to use the Lowenstein-Jensen medium within a relatively short period after preparation. The preparation of the Lowenstein-Jensen medium is quite time consuming and, therefore, the use of the Lowenstein-Jensen medium has mainly been restricted to organizations which conduct sufficient tuberculosis test as to justify the repeated time-consuming preparations of the Lowenstein-Jensen medium. The occasional tester or the smaller institution cannot economically test for tuberculosis, due to the difficulty and expense of frequently preparing fresh medium.

A basic ingredient in the Lowenstein-Jensen medium is fresh whole eggs, e.g., eggs no older than three days. The medium must be prepared in a specific manner with specific nutrients/salts/inhibitors and fresh whole eggs, as is well known in the art. If the medium is not used within a relatively short time after preparation (even if refrigerated), the results obtained therewith are questionable. Attempts in the art at extending the useful life of a prepared Lowenstein-Jensen medium have not met with success and the most common expedient is to pre-mix the dry ingredients in a sterile manner and to place the fresh eggs in the dry mixture when the medium is to be prepared.

In the parent application, identified above, it is disclosed that freshly prepared Lowenstein-Jensen medium can be stabilized for extended ambient storage by spray-drying that freshly prepared medium under such specific and critical conditions as to avoid deterioration of the dried product. The spray-drying technique is taught to be unique in drying procedures, in this regard, i.e. as opposed to tray drying, roller drying, etc.. It is also taught that the Lowenstein-Jensen medium, spray-dried in that specific manner, will remain storage stable for extended periods of time and may be conveniently reconstituted with water for testing for tuberculosis organisms. That parent application also teaches that even after prolonged periods of storage, the spray-dried medium can be reconstituted and used for testing for tuberculosis organisms. The primary basis of that conclusion was in vitro testing where the dried medium, after prolonged storage periods, was reconstituted and was shown to be capable of growing *M. tuberculosis* organisms.

However, clinical trials of the spray-dried Lowenstein-Jensen medium have discovered that the reconstituted spray-dried material is not as accurate as the freshly prepared medium. Indeed, the accuracy occasioned by the reconstituted spray-dried medium is decreased to approximately 75% as accurate as the fresh medium.

It has now been determined that the population of tuberculosis organisms in a clinical specimen may be considerably lower than the normal populations encountered in stock cultures used in in vitro testing. Thus, while the spray-dried material is quite accurate in testing specimens with relatively large numbers of tuberculosis organisms therein, its accuracy substantially decreases when the population of the organisms decreases. This is often the case encountered in clinical specimens and, hence, decreased accuracy in the clinical situation is experienced.

It has also been discovered that in order to simulate the problem encountered in clinical situations by in vitro testing, the normal stock solutions of tuberculosis organisms must be diluted in the order of at least $10^3$. If adequate growth takes place at these low dilutions, then the medium is satisfactory for clinical use.

OBJECTS OF THE INVENTION

It is therefore an object of the invention to provide storage-stable Lowenstein-Jensen medium which may be stored at ambient conditions for prolonged periods of time without significant deterioration thereof. It is another object of the invention to provide such storage-stable Lowenstein-Jensen medium in a dried form. It is a further object of the invention to provide such dried Lowenstein-Jensen medium in a form which can be easily reconstituted with water by simple mixing. It is a further object of the invention to provide such storage-stable Lowenstein-Jensen medium which, additionally, upon reconstitution will provide clinical accuracy equal to freshly prepared Lowenstein-Jensen medium. Finally, it is another object of the invention to provide methods for producing such storage-stable Lowenstein-Jensen medium. Other objects will be apparent from the following disclosure and claims.

BRIEF DESCRIPTION OF THE INVENTION

It has now been quite unexpectedly discovered that Lowenstein-Jensen medium may be stabilized for sustained preservation by freeze drying the medium in a conventional freeze dryer and that the reconstituted freeze-dried medium exhibits tuberculosis testing accuracy equal to freshly prepared Lowenstein-Jensen medium.

Thus, there is provided a dry, storage-stable Lowenstein-Jensen medium which may be reconstituted with water to provide a medium suitable for use in tuberculosis testing, comprising a freeze-dried form a Lowenstein-Jensen medium, the moisture content of the freeze-dried medium being less than 8% by weight and the reconstituted freeze-dried medium exhibits tuberculosis testing accuracy equal to that of freshly prepared Lowenstein-Jensen medium.

There is also provided a method for preparing the dry, storage-stable Lowenstein-Jensen medium, which comprising mixing fresh whole eggs and Lowenstein-Jensen nutrients, salts and inhibitors in Lowenstein-Jensen proportions, freezing the mixture and subjecting the mixture to sufficiently reduced pressure that sublimation of liquid in the frozen mixture occurs and until a moisture content of the mixture of 8% or less is reached.

DETAILED DESCRIPTION OF THE INVENTION

The initial medium prepared or freeze drying will be the same as a conventional Lowenstein-Jensen medium. There are a number of variations on the procedures for preparing a Lowenstein-Jensen medium or a modification thereof, but generally, fresh whole eggs are aseptically combined with Lowenstein-Jensen nutrients, salts, stabilizers, inhibitors, thickeners, etc., in Lowenstein-Jensen proportions to provide a well-blended mixture. Thereafter, the mixture is inspissated at less than 80°–90° C. for about 45 minutes.

A commonly used procedure is that of cleaning fresh eggs in 5% soda and soap solution, rinsing thoroughly with water, aseptically breaking the eggs into a sterile flask containing glass beads, adding the nutrients, salts, etc., shaking to form a uniform mixture or emulsion, placing the mixture in slant tubes and autoclaving the tubes in a slanted position at 80°–90° C. for 45 minutes. Sterility is checked by incubating the tubed medium slants at 37° C. The slants are stored under refrigeration.

Irrespective of the specific procedure used, after the medium has been prepared, according to the present invention, it is introduced into a conventional freeze-drying apparatus and freeze dried under conventional conditions. The particular conventional freeze drying conditions may be chosen as desired and it is only important that the dried medium have a moisture content of 8% by weight or less.

However, quite conveniently, the freeze drying process may be conducted as follows: Firstly, the conventional Lowenstein-Jensen salts are added to the appropriate portion of water with or without heat (up to the boiling point of the water) to aid mixing. Asparagine is then added, preferably to the heated mixture, with stirring to dissolve the same. After the salts, etc. are fully dissolved, the solution is cooled and potato flour is then added (preferably at tepid temperatures to aid in mixing). After a homogeneous mixture is obtained, the temperature is raised to heat the potato flour, e.g. 150°–190° F. for 1-30 minutes. That mixture is then cooled to at least below 130° F., and the fresh whole eggs are added thereto. Alternatively, a potato flour mixture and a salt/nutrient mixture may be separately prepared and added together. In any event, the total mixture of the nutrients/salts/inhibitors, etc. and potato flour is prepared before adding the fresh whole eggs.

After the eggs are homogeneously dispersed in the mixture, the mixture is placed on trays and subjected to reduce temperatures for freezing thereon. While these temperatures are not critical, the lower the temperature the faster the process. For this reason, temperatures at least below 25° F. are preferred, e.g., 10° to −20° F.

The frozen slab of Lowenstein-Jensen medium is removed from the trays and broken or crushed to provide increased surface area. Ideally, the average particle size will be between 1/16 inch and ½ inch, usually between ⅛ inch and ⅜ inch. A good average size is about ¼ inch, since this avoids packing of the particles and yet provides sufficient surface area for effective freeze drying.

The crushed frozen Lowenstein-Jensen medium is then poured into conventional freeze-drying trays (preferably covered with a polyethylene lining) to provide a layer of from ¼ to 1 inch thick, usually about ½ inch thick. These trays are placed in a conventional freeze dryer so that the trays are suspended in juxtaposition to heated shelves. A vacuum is drawn on the trays, e.g. 100 to 600 microns, usually between 100 and 200 microns. Oil which is recirculated through the shelves for temperature control is adjusted such that the temperature of the surface of the layer of the crushed Lowenstein-Jensen medium, as usually measured by thermocouples placed thereon, does not exceed at any one point a temperature of 130° F. While freeze drying is conventionally conducted at temperatures of the surface of the layer of material in excess of 150 or even 160° F., this cannot be practiced with the present invention. It has been found that if temperatures at the surface of the layer exceeds about 130° F., then the resulting freeze-dried product is substantially deteriorated in its accuracy of turberculosis testing. Othersise, the freeze-drying technique is as conventionally practiced. The moisture content of the dried product, however, must be about 8% or less and preferably less than 7%. Usually, the moisture content of the freeze-dried product will be between 3% and 5%.

The dried powder is recovered from the freeze dryer in the conventional manner and may then be packaged in any container desired so long as the container prevents ambient contamination. Thus, the dried powder may be simply packaged in plastic or glass jars, flexible film, blister packages, twisted plastic bag packages, foil packages, wax paper packages and the like. While it is not required that the package be hermetically sealed, this is preferred (or like provisions be made), which provides that ambient contamination be substantially eliminated by the packaging method. The elimination of ambient contamination is not in connection with the stabilized Lowenstein-Jensen medium itself, but in connection with unknown organisms which might be introduced into the reconstituted powder when used in testing for tuberculosis.

The dried and packaged powder need not be stored under special temperatures, and ambient temperatures are quite acceptable. However, extreme temperatures should be avoided for obvious reasons. Accordingly, it is preferred that the powder not be subjected to freezing temperatures, nor is it preferred that the powder be stored at temperatures above 120° F., preferably less than 115° F., although neither of these extreme temperatures will adversely affect the powder unless the powder remains at those extreme temperatures for prolonged periods. On the other hand, the powder may be stored for prolonged periods of time at ambient temperatures without significant deterioration thereof, i.e. at least six months and up to one year, although as a precautionary measure and as a safety factor, it is preferred that the powder be reconstituted and used within 8 to 10 months of the drying time.

The powder may be reconstituted simply by mixing with water. Of course, it is preferred that the mixing be under sterile conditions and that the water be both sterilized and distilled. Inspissation at 80° C. to 90° C. for 1 hour may be used if desired. The amount of powder which is reconstituted in water can vary considerably, but it is preferred that the amount which is reconstituted corresponds to that which will produce the same solids content as the original freshly prepared Lowenstein-Jensen medium. Thus, the solid content of the reconstituted medium can vary from as low as 10% to as high as 20% by weight, but the preferred solid content will be between about 11% and 17%, especially between 13% and 15%.

Reconstitution can be accomplished without any special technique or equipment, and simple mixing is quite adequate. Thus, the dried powder and water may be simply hand mixed or mixed with a conventional laboratory stirrer until dissolution thereof takes place. The mixing may be at ambient temperatures or slightly depressed or elevated temperatures and no special consideration in this regard is required. Accordingly, temperatures above the freezing point of water and as high as 120° F. can be used for preparing the reconstituted mixture. However, there is no special advantage obtained by such variation in the temperature of the water for reconstitution, and ambient water is quite satisfactory.

For purposes of the present specification, the Lowenstein-Jensen medium is defined as a medium for the growth of tuberculosis organisms (*Mycobacterium tuberculosis*) and consists essentially of fresh whole egg, Lowenstein-Jensen defined nutrient, salts and inhibitors in Lowenstein-Jensen defined proportions, all of which is well known to the art. If desired, stabilizers, thickeners, dyes and like non-essential ingredients may be used. The specific nutrients/salts/inhibitors and the ratios with the fresh whole egg may vary, as is known in the art. Thus, all combinations of fresh whole egg/inhibitors/nutrients/ salts suitable for growing tuberculosis organisms are intended to be embraced by the present disclosure and claims. A typical Lowenstein-Jensen formulation, however, will contain from about 0.5% to about 3% salts. The amount of water will be from about 2% to about 10% for dispersing and dissolving the salts, but more generally from about 4% up to about 8%. Very often the amount of water will be about 5 or 6%. Additional water may be used if desired for easy dispersement and dissolution of the salts since this only goes to diluting the concentration of the Lowenstein-Jensen medium. Higher dilutions are not preferred, however, and generally speaking, no more than 15% by weight of the medium will be added water. The remainder of the medium will be essentially fresh eggs, but if desired, aside from the usual inhibitors, thickeners, viscosity control agents and the like may be added. Thus, typically, the medium will also contain up to 7% of potato flour, especially between 1% and 6% and more generally between 4% and 5%. Glycerol is not used in the freeze-dried powder since it will interfere with freezing, but it may be added during reconstitution of the dried powder at typical concentrations. An inhibitor or a dye or a material which will function in both manners is also generally added to the medium. Thus, 0.1% to about 1% of an inhibitor and/or dye, and more generally 0.5% to 1% Malachite Green is commonly used in a Lowenstein-Jensen medium for this purpose. The typical salts used in the medium generally contain magnesium and phosphorous, as well as potassium and the particular combination of these salts is not narrowly critical. However, as a typical example, monopotassium phosphate, magnesium sulfate, and magnesium citrate may be used. Also, typically, asparagine is used as a very convenient nutrient. Asparagine is an amino acid found in the sprouts of many weeds and has the formula $NH_2 \cdot CH \cdot (COOH) \cdot (CH_2 CONH_2) \cdot H_2O$.

It has been found that the present freeze-dried Lowenstein-Jensen medium is equal in accuracy of tuberculosis testing to freshing prepared Lowenstein-Jensen medium, while the spray-dried Lowenstein-Jensen medium of the above-identified parent application has a decrease of accuracy in a clinical setting to about 75%. The reason for this difference is not known and it is, indeed, surprising that the freeze-dried medium functions in such a superior manner as compared with the spray-dried medium. Investigations into the physical differences between the spray-dried and freeze-dried medium have not provided reasons for these differences. While the spray-dried medium is more nearly in the form of spherical particles and the like, while the freeze-dried material is more normally in the form of flaked particles and the like, differences in ability to dissolve, disperse, etc. do not account for the differences in clinical performance.

The experimental work which culminated in the parent application was based, primarily, on in vitro testing of the spray-dried medium. It has subsequently been discovered that the population of tuberculosis organisms normally equilibriumly established in stock solutions of the organisms is so great that no difference in accuracy of the spray-dried medium and the freshly prepared medium can be observed when testing with these stock solutions in in vitro circumstances. However, the population of tuberculosis organisms often encountered in a clinical specimen is substantially lower than that of the stock solution. Hence, for these clinical specimens, the spray-dried medium is not sufficient to detect the presence of low populations of tuberculosis organisms, while the freshly prepared Lowenstein-Jensen medium is sufficiently accurate for those specimens. It can therefore be seen that the use of the spray-dried material places the clinician at a distinct disadvantage, as opposed to the use of a freshly prepared Lowenstein-Jensen medium.

It is now discovered that if classical serial dilutions are made that a dilutions between about $10^4$ and $10^5$ in vitro testing can essentially simulate the difficult clinical specimens discussed above. These dilutions are made in the traditional manner of inoculating a test culture with stock solution, incubating and transferring a portion of the incubated culture to another culture such that a ten-fold dilution occurs. That culture is then incubated and a further transfer to a new culture is made with a subsequent ten-fold dilution, etc.. With this in vitro testing, the present freeze-dried material remains accurate at $10^4$ and $10^5$ dilutions, the same maximum dilutions of the freshly prepared Lowenstein-Jensen medium.

This in vitro testing has also been confirmed for the freeze-dried material by clinical testing where the accuracy of the freeze-dried medium is the same as the accuracy of the freshly prepared Lowenstein-Jensen medium.

Accordingly, the present invention provides a most distinct improvement over the spray-dried medium of the parent application and also provides the art with the advantage of a storage-stable easily-reconstituted Lowenstein-Jensen medium. Thus, the objects of the invention have been achieved.

The invention will be illustrated by the following examples, where all percentages and proportions are by weight, unless otherwise indicated, but it is to be clearly understood that the invention is not limited thereto and is fully applicable to the foregoing disclosure.

EXAMPLE 1

| The following salts were added to water: | |
|---|---|
| monopotassium phosphate | 2.06 lbs. |
| magnesium sulfate | 90 g. |
| magnesium citrate | 225 g. |
| water(de-ionized) | 59.5 gal. |

The solution was prepared by adding the salts to the water in a 200 gallon stirred kettle. The temperature was brought to 200° F. and 625 grams of asparagine was added and mixed at that temperature for 20 to 30 minutes. After mixing, the solution was cooled to below 100° F.

To the cooled solution was added 25 lbs. of potato flour in small increments with constant agitation to avoid lumping. Thereafter, the mixture was heated to 180° F., stirred at that temperature for 20 minutes and then cooled to below 130° F.

Thereafer 840 lbs. of whole homogenized eggs (prewashed) were added to the solution and thoroughly mixed.

150 grams of Malachite green was added and after mixing, the solution was placed in polyethylene lined trays and frozen in a conventional freeze-drying apparatus at about −10° F. (Stokes-Eastern Freeze-Dry Corp). After freezing, the resulting slabs were crushed to an average particle size of ¼ inch. The trays were filled with the crushed material to form a layer of about ½ inch thick. A vacuum of about 100 to 200 microns was pulled on the trays and the recirculated oil in the shelves of the dryer was adjusted so that the maximum temperature of the surface of the layers was below about 120° F. Drying was continued until the product had moisture contents of between 3 and 5%.

The dry product was pulverized to a free-flowing powder and packaged in air-tight containers.

EXAMPLE 2

Product of Example 1 was reconstituted with distilled water by mixing and slants thereof were prepared in the same manner as conventionally practiced with fresh Lowenstein-Jensen medium. The slants were inoculated with bacteria taken from a stock culture of *Mycobacterium tuberculosis*. After incubation, a 10 fold dilution of the resulting culture was made and that diluted culture was incubated. This procedure was serially repeated to determine the maximum dilution of organism which would grow on the reconstituted freeze dried Lowenstein-Jensen medium. A total of 12 simultaneous tests were conducted and it was determined that between the $10^4$ and $10^5$ dilutions, no growth took place. This test determines the sensitivity of the freeze-dried medium for detecting low population numbers of the tuberculosis organism.

The same test was repeated with commercially available, freshly prepared and pre-tubed Lowenstein-Jensen medium (Difco brand). In this case growth also ceased between the $10^4$ and $10^5$ dilutions.

Thus, it can be seen that from an in vitro point of view the freeze-dried Lowenstein-Jensen medium is equal to the freshly prepared medium.

EXAMPLE 3

Clinical trials were made with:

(a) Commercially available, freshly prepared are pretubed Lowenstein-Jensen medium (Difco brand);

(b) reconstituted freeze-dried medium of Example 1; and (c) reconstituted spray-dried medium of Example 1, test 1, of that parent application.

The freshly prepared medium was considered the standard and the freeze-dried medium and the spray-dried medium were compared with the standard in terms of the ability to detect the presence of tuberculosis organisms in clinical samples. This shows an overall accuracy of the medium, as compared with the freshly prepared medium.

No difference between the freshly prepared medium (Difco brand) and the freeze-dried medium was observed, but the spray-dried medium was only 72% as accurate as the freshly prepared medium and the freeze-dried medium.

EXAMPLE 4

In order to demonstrate the storage properties of the dried powder, samples of the product of Example 1 were stored in a tightly capped container for the periods of 1,2,3,4,5,6,10 and 12 months. At the end of each storage period, the sample for that period was reconstituted to provide a medium with the same solid content as was originally present in the medium prior to freeze drying. Slants of each sample were tested by inoculating with tuberculosis organisms. At the end of an incubation period of 2 weeks, the samples were examined and each showed a positive culture of *M tuberculosis.* Accordingly, this example illustrates that the present freeze-dried medium can be stored for prolonged periods of time and thereafter easily reconstituted for use in tuberculosis testing.

EXAMPLE 5

The procedure of Example 4 was serially repeated with the following organisms instead of the *M. tuberculosis: Mycobacterium avium, M. bovis, M. kansasii, M. fortutium, M. intracellulare,* and *M. scrofulaceum.* Each organism was provided from a stock culture. The freeze-dried sample had been stored for 1 year and the incubation period was 3 weeks. Each test was compared with pre-tubed Lowenstein-Jensen medium (Difco brand). The growths on the reconstituted medium and the pre-tubed medium were equal.

This example shows that the stored, dry medium is effective for a wide range of Mycobacterium, which are also indicated in tuberculosis-type diseases, and may be so used. It also shows that the present medium is most satisfactory as a growth medium for the genus Mycobacterium.

Modifications of the foregoing can easily be accomplished by those skilled in the art and such modifications are intended by the specification. Thus, the invention is limited only by the following claims:

What is claimed is:

1. A method for preparing a dry, storage-stable Lowenstein-Jensen medium which may be reconstituted with water to provide a medium suitable for use in tuberculosis testing, comprising mixing fresh whole eggs and Lowenstein-Jensen nutrients, inhibitors and salts having metal ions selected from the group consisting of magnesium, phosphorous and mixtures thereof potassium, freezing the mixture of eggs and salts at temperatures below 25° F. and subjecting the mixture to drying at substantially reduced pressure and at temperatures wherein layers at the upper surface of the frozen mixture do not exceed 130° F. during the drying, and wherein sublimation of liquid in the frozen mixture occurs until a moisture content of the mixture of 8% or less is obtained.

2. The method of claim 1 wherein the frozen Lowenstein-Jensen medium is crushed to an average particle size of between 1/16 inch and ½ inch, prior to drying, and layers of the crushed frozen medium are dried.

3. The method of claim 1 wherein the moisture content is reduced to 6% or less.

4. The method of claim 1 wherein the dried medium is packaged to avoid ambient contamination.

5. The method of claim 4 wherein the packaged medium is stored at ambient temperatures.

6. The methods of claim 5 wherein the packaged medium is stored for up to one year.

7. The method of claim 1 wherein the medium is reconstituted by mixing with water.

8. The product produced by the process of claim 1.

9. The product of claim 8 having a moisture content of 6% or less.

10. The product of claim 8 in an air-tight package.

* * * * *